US008834480B2

(12) United States Patent
Hudak, Jr. et al.

(10) Patent No.: US 8,834,480 B2
(45) Date of Patent: Sep. 16, 2014

(54) ADAPTER FOR EXPLANT SYSTEM

(75) Inventors: John J. Hudak, Jr., Winona Lake, IN (US); Sarah M. Gedney, Fort Wayne, IN (US); Timothy P. Dolan, Goshen, IN (US)

(73) Assignee: Zimmer, Inc., Warsaw, IN (US)

( * ) Notice: Subject to any disclaimer, the term of this patent is extended or adjusted under 35 U.S.C. 154(b) by 219 days.

(21) Appl. No.: 13/350,027

(22) Filed: Jan. 13, 2012

(65) Prior Publication Data

US 2012/0184964 A1    Jul. 19, 2012

Related U.S. Application Data

(60) Provisional application No. 61/433,347, filed on Jan. 17, 2011.

(51) Int. Cl.
*A61B 17/88* (2006.01)
*A61F 2/30* (2006.01)
*A61F 2/46* (2006.01)

(52) U.S. Cl.
CPC ..... *A61F 2/4609* (2013.01); *A61F 2002/30332* (2013.01); *A61F 2002/4619* (2013.01); *A61F 2002/30378* (2013.01); *A61F 2002/30354* (2013.01); *A61F 2002/30405* (2013.01); *A61F 2002/30487* (2013.01)
USPC .......................................... 606/91; 606/86 R

(58) Field of Classification Search
USPC ...................... 606/86 R, 90–91, 99
See application file for complete search history.

(56) References Cited

U.S. PATENT DOCUMENTS

| 4,135,517 | A | * | 1/1979 | Reale .......................... 606/86 R |
| 5,830,215 | A | | 11/1998 | Incavo et al. |
| 5,919,195 | A | | 7/1999 | Wilson et al. |
| 6,022,357 | A | | 2/2000 | Reu et al. |
| 6,059,833 | A | | 5/2000 | Doets |
| 6,063,123 | A | | 5/2000 | Burrows et al. |
| 6,063,124 | A | | 5/2000 | Amstutz |
| 6,152,930 | A | | 11/2000 | Mastrorio |

(Continued)

FOREIGN PATENT DOCUMENTS

| CN | 103313680 A | 9/2013 |
| WO | WO2007/113607 A1 | 10/2007 |

OTHER PUBLICATIONS

International Search Report and Written Opinion mailed Mar. 27, 2012 in the related International Patent Application No. PCT/US2012/021250.

(Continued)

*Primary Examiner* — Nicholas Woodall
*Assistant Examiner* — Larry E Waggle, Jr.
(74) *Attorney, Agent, or Firm* — Schwegman Lundberg & Woessner, P.A.

(57) ABSTRACT

The present disclosure provides an improved osteotome instrument for removing an acetabular cup from an acetabulum, including an explant adapter connectable to an elongated handle shaft of the instrument. The explant adapter is sized and shaped to connect any one of a set of a plurality of different sized interchangeable pivot elements, such as spherical heads, to the osteotome instrument for use in removing the acetabular cup from the acetabulum. The pivot heads may be relatively large diameter pivot heads.

18 Claims, 9 Drawing Sheets

(56) References Cited

U.S. PATENT DOCUMENTS

| | | |
|---|---|---|
| 6,395,005 B1 | 5/2002 | Lovell |
| 6,565,575 B2 | 5/2003 | Lewis |
| 2002/0116007 A1* | 8/2002 | Lewis ............................ 606/99 |
| 2006/0200165 A1 | 9/2006 | Tulkis |
| 2008/0195111 A1* | 8/2008 | Anderson ....................... 606/90 |
| 2008/0255568 A1* | 10/2008 | Tornier et al. ................... 606/91 |
| 2010/0161069 A1* | 6/2010 | Ragbir ....................... 623/22.11 |
| 2010/0262155 A1* | 10/2010 | Teeny et al. ..................... 606/99 |

OTHER PUBLICATIONS

Zimmer Metasul LDH Large Diameter Head with Durom Acetabular Component, Surgical Technique, Zimmer, Inc. 2007, 2008.

Zimmer Explant Acetabular Cup Removal System, Surgical Technique, Zimmer, Inc. 2002, 2005, 2007.

"International Application Serial No. PCT/US2012/021250, International Preliminary Report on Patentability mailed Jul. 25, 2013", 8 pgs.

* cited by examiner

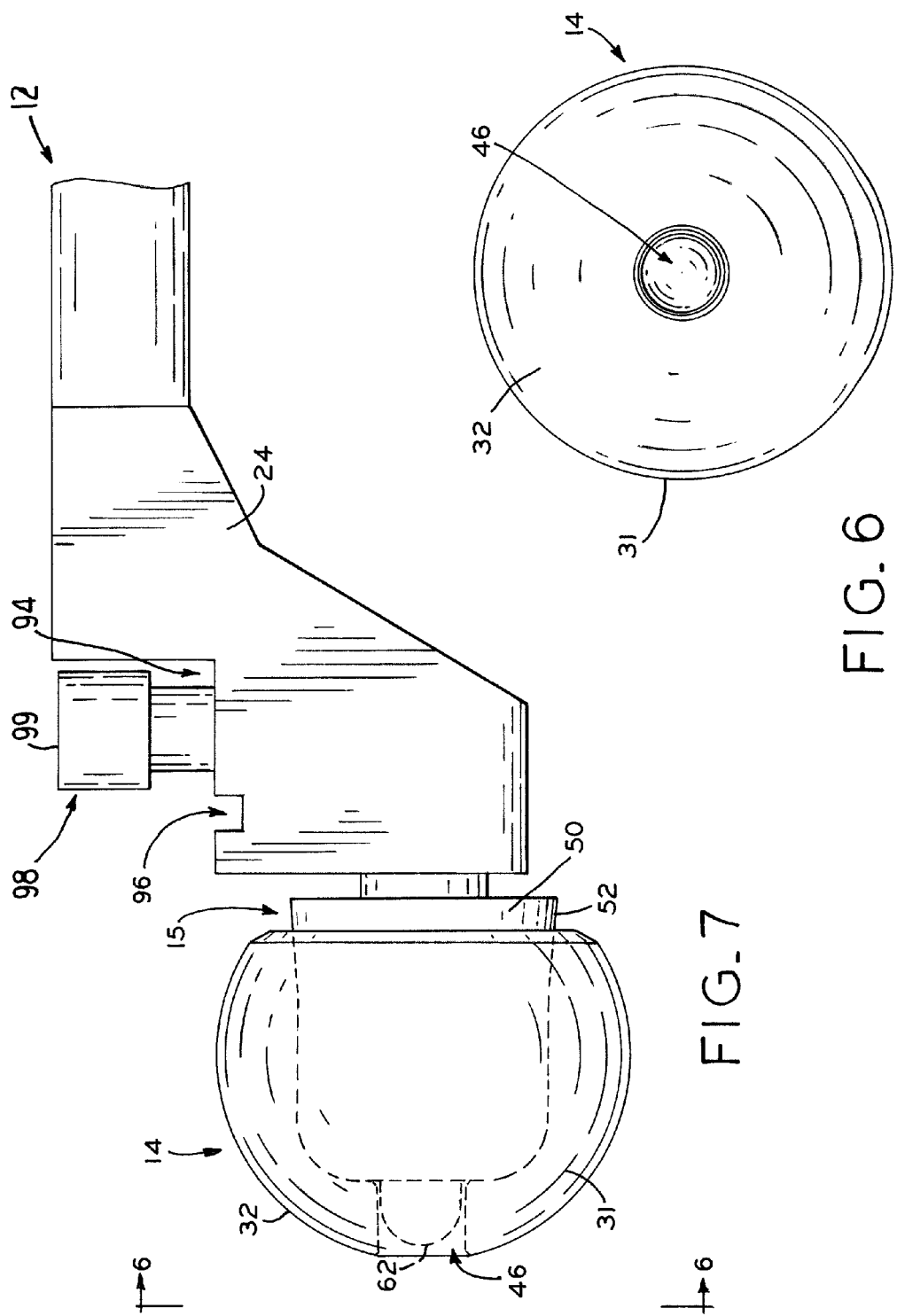

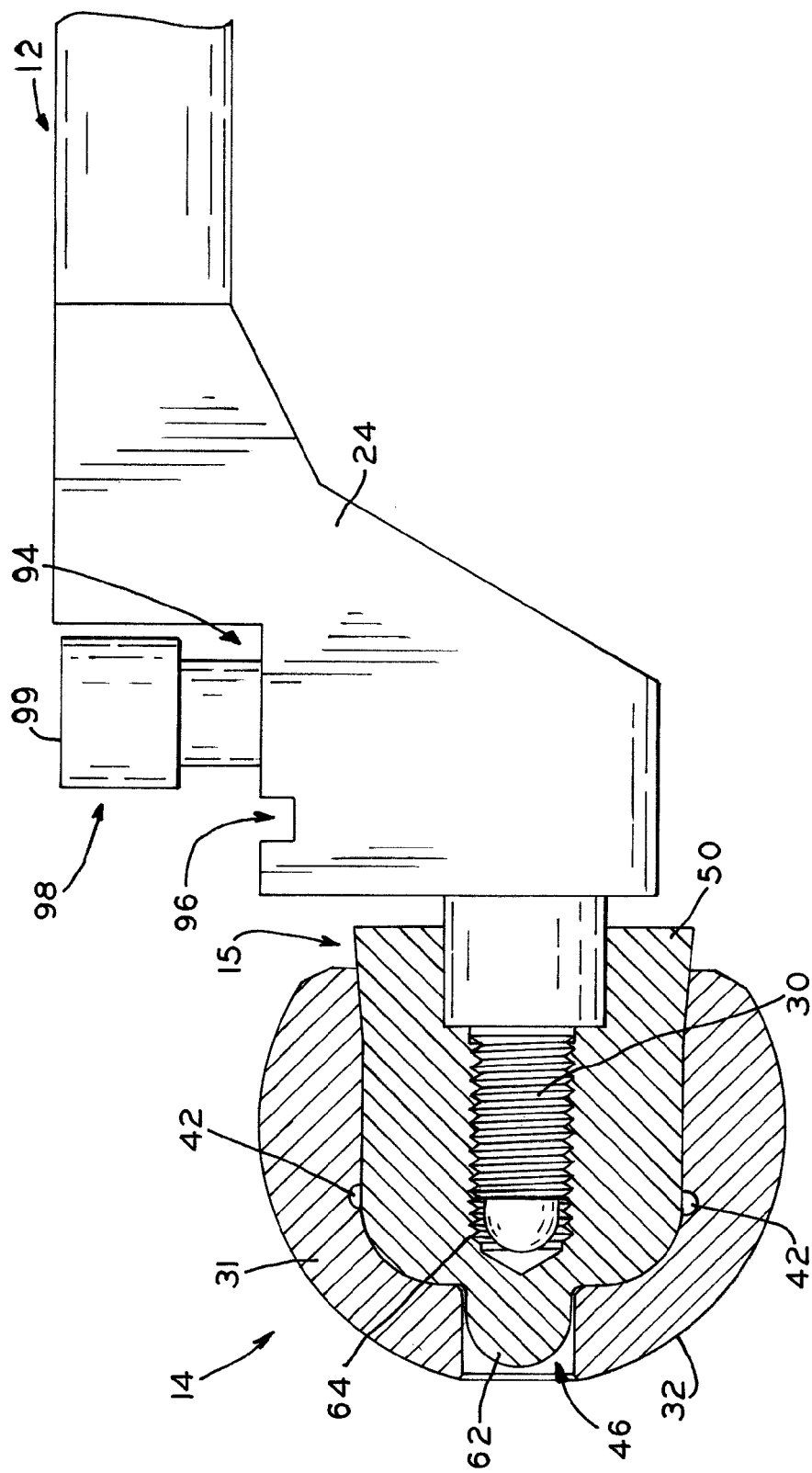
FIG_8

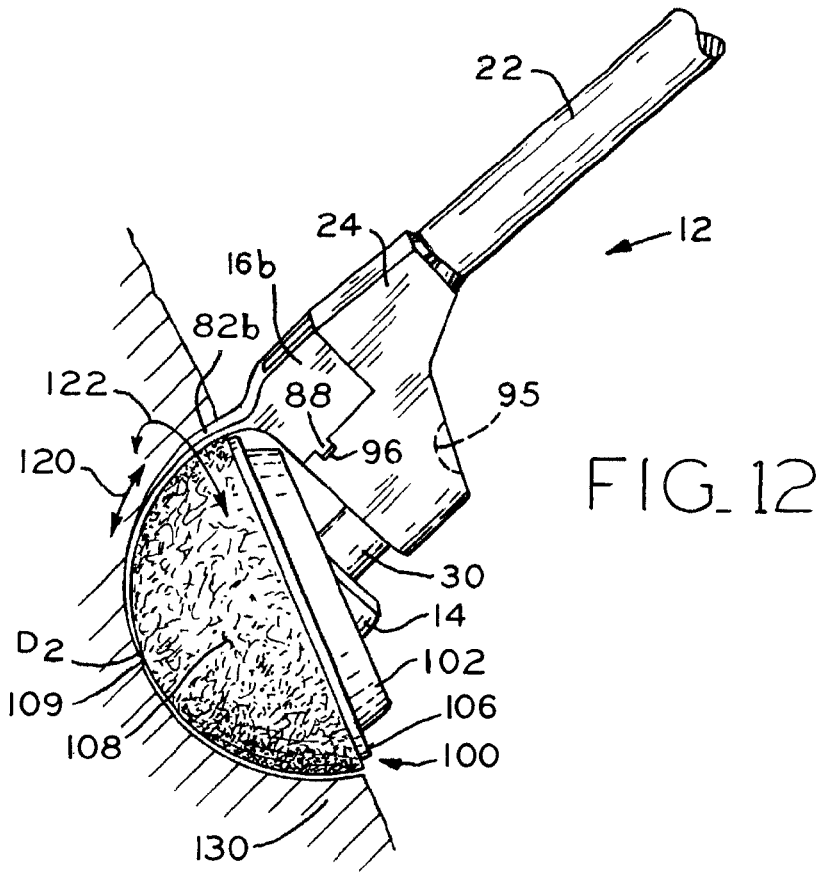
FIG. 12
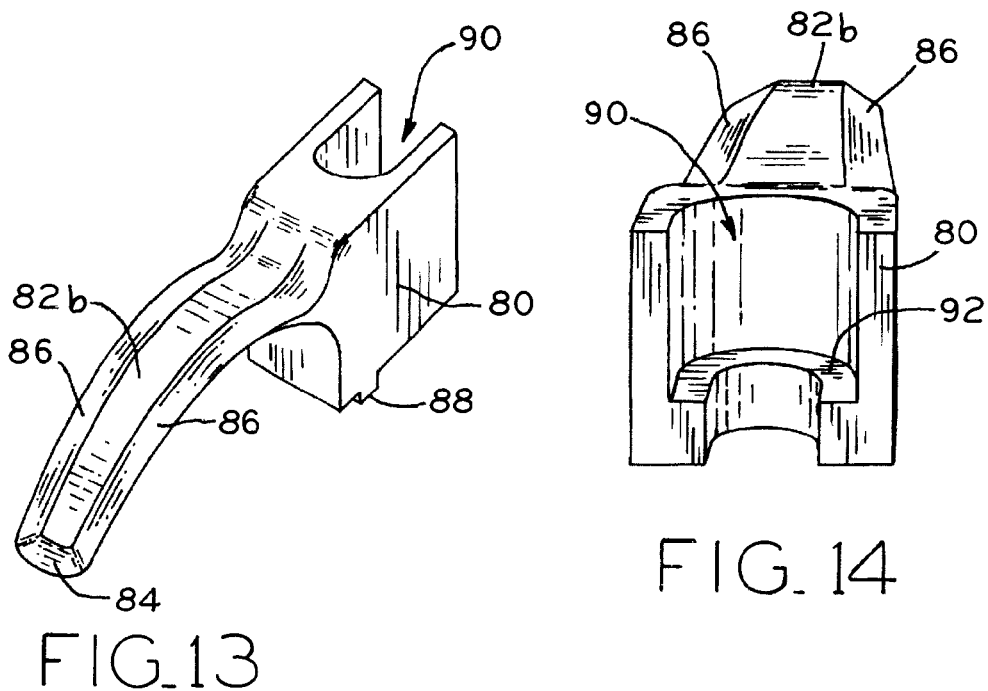
FIG. 13
FIG. 14

ADAPTER FOR EXPLANT SYSTEM

CROSS REFERENCE TO RELATED APPLICATIONS

This application claims the benefit under Title 35, U.S.C. §119(e) of U.S. Provisional Patent Application Ser. No. 61/433,347, entitled ADAPTER FOR EXPLANT SYSTEM, filed on Jan. 17, 2011, the entire disclosure of which is expressly incorporated by reference herein.

BACKGROUND

1. Field of the Disclosure

The present disclosure relates generally to prosthetic hip joints, which include an acetabular cup positioned within a patient's acetabulum to serve as the socket for the hip joint. More particularly, the present disclosure relates to an explant system for removing the acetabular cup from the acetabulum.

2. Description of the Related Art

Prosthetic hip joints generally include a femoral component and an acetabular component, the acetabular component including an acetabular cup positioned in a patient's acetabulum which serves as the socket for the hip joint and receives the head of a femoral component. During a prosthetic hip joint revision procedure, the acetabular cup is removed from the acetabulum and replaced with a new acetabular cup.

An acetabular cup may be removed from an acetabulum in accordance with the method and apparatus described in U.S. Pat. No. 6,565,575 issued May 20, 2003, entitled "Method and Apparatus for Removing an Acetabular Cup," the disclosure of which is hereby expressly incorporated herein by reference. U.S. Pat. No. 6,565,575 discloses a surgical kit including an osteotome instrument having an elongated handle shaft terminating in a head portion, a plurality of interchangeable osteotomes having curved blades of different lengths, and pivot elements, such as spherical heads, which may be attached to the head portion of the instrument. In use, the spherical head of the osteotome instrument is seated within a recess of an acetabular cup liner such that the end of the osteotome blade is disposed closely adjacent the rim of the acetabular cup. Thereafter, the handle shaft of the osteotome instrument may be pivoted and/or rotated to make several cuts with the curved osteotome blade which are closely adjacent the outer hemispherical surface of the acetabular cup, until the acetabular cup may be removed from the acetabulum.

An internally-threaded, entirely frustoconical metal adapter has been used with the instrument of the above-referenced U.S. Pat. No. 6,565,575. After dislocating a prosthetic hip joint, the metal implant head is disengaged from the hip stem of the hip prosthesis, and the adapter is fitted within the frustoconical bore of the metal implant head in which the trunion of the hip stem was previously fitted. Thereafter, the threaded end of the instrument of the above-referenced U.S. Pat. No. 6,565,575 is threaded into the adapter and the acetabular cup is removed using the implant head in articulation with the acetabular cup.

Disadvantageously, this arrangement relies on use of the implant head of the hip prosthesis having the acetabular cup which is to be removed, and requires multiple adapters of varying size that are dimensioned to be compatible with the various sizes of implant heads of the hip prostheses.

SUMMARY

The present disclosure provides an improved osteotome instrument for removing an acetabular cup from an acetabulum, including an explant adapter connectable to an elongated handle shaft of the instrument. The explant adapter is sized and shaped to connect any one of a set of a plurality of different sized interchangeable pivot elements, such as spherical heads, to the osteotome instrument for use in removing the acetabular cup from the acetabulum. The pivot heads may be relatively large diameter pivot heads.

In one aspect of the present disclosure, an instrument for removing an acetabular cup from an acetabulum includes a handle; a blade connectable to the handle; an adapter connectable to the handle in spaced relationship from the blade, the adapter having an exterior profile including a first cylindrical portion and a first frustoconical portion; and a pivot element connectable to the adapter and dimensioned to be received within an acetabular cup, the pivot element having an interior profile including a second cylindrical portion and a second frustoconical portion, the first and second frustoconical portions dimensioned complementary to one another to form a taper lock, and the first and second cylindrical portions dimensioned to interference fit with one another, upon receipt of the adapter within the pivot element.

In another aspect of the present disclosure, an instrument for removing an acetabular cup from an acetabulum includes a handle; a blade connectable to the handle; an adapter connectable to the handle in spaced relationship from the blade, the adapter having an exterior profile and a distal end including a protrusion; and a pivot element connectable to the adapter and dimensioned to be received within an acetabular cup, the pivot element having an interior profile dimensioned complementary to the exterior profile of the adapter for receipt of the adapter within the pivot element, the pivot element further including a cavity in which the protrusion is receivable.

In a further aspect of the present disclosure, a kit for removing an acetabular cup from an acetabulum includes an instrument having a handle; a blade connectable to the instrument; a metal adapter connectable to the instrument in spaced relationship from the blade, the adapter having an exterior profile; a first pivot element made of a polymeric material and connectable to the adapter, the first pivot element having a first diameter and dimensioned to be received within an acetabular cup, the first pivot element defining an interior profile, the exterior profile of the adapter dimensioned for receipt within the interior profile of the first pivot element; and a second pivot element made of a polymeric material and connectable to the adapter, the second pivot element having a second diameter different from the first diameter and dimensioned to be received within an acetabular cup, the second pivot element defining an interior profile, the exterior profile of the adapter dimensioned for receipt within the interior profile of the second pivot element.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 6 is a front elevation view of a spherical head in accordance with the present disclosure;

FIG. 7 is an assembled view showing the explant adapter of FIG. 2 attached to the threaded shaft of the head portion of the osteotome instrument of FIG. 2, and a spherical head secured to the explant adapter of FIG. 2;

FIG. 8 is another assembled view showing the explant adapter of FIG. 2 attached to the threaded shaft of the head portion of the osteotome instrument of FIG. 2, further showing the adapter and spherical head in cross-section;

FIG. 12 is a partial sectional view showing the osteotome instrument of FIG. 10 with an osteotome having a long blade attached thereto, the osteotome blade cutting bone adjacent the acetabulum to a second depth at the apex of the acetabular cup;

FIG. 13 is a front perspective view of an interchangeable osteotome having a long blade, for use with the osteotome instrument of FIGS. 9-12; and FIG. 14 is a rear perspective view of the interchangeable osteotome of FIG. 13.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
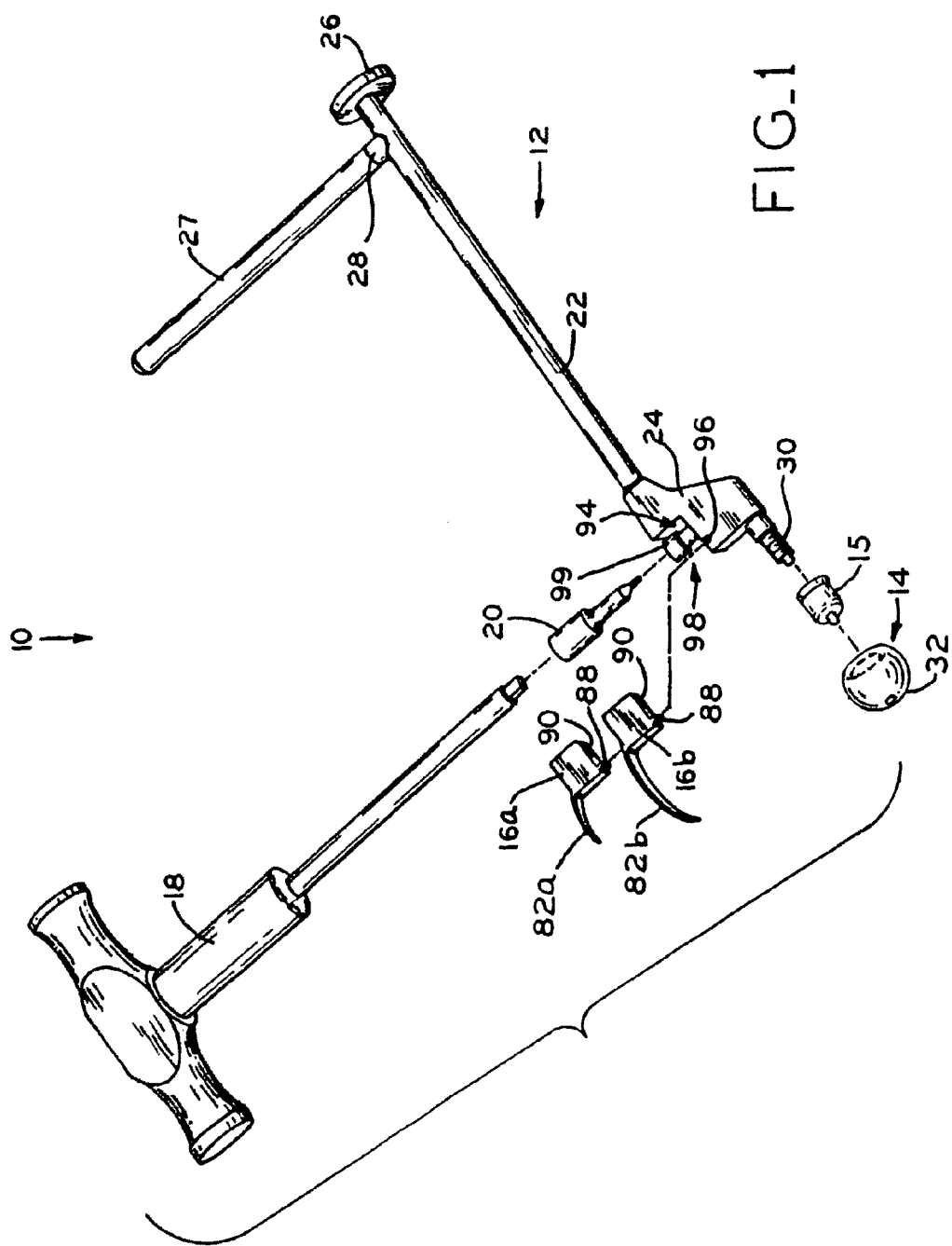
FIG. 1 is a perspective view of the components of a surgical kit in accordance with the present disclosure.

Referring to FIG. 1, surgical kit 10 is shown, which generally includes osteotome instrument 12, one of a plurality of interchangeable pivot elements, such as spherical head 14, explant adapter 15 for connecting spherical head 14 to osteotome instrument 12, a plurality of interchangeable osteotomes 16a, 16b, torque wrench 18, and osteotome adapter 20 for securing osteotomes 16a, 16b to osteotome instrument 12. Osteotome instrument 12 includes handle shaft 22 having head portion 24 at a distal end thereof, and impaction head 26 threaded onto a proximal end thereof. Handle lever 27 is threaded into shoulder 28 of handle shaft 22. Handle shaft 22 and handle lever 27 may be grasped to manipulate osteotome instrument 12, as described in further detail below.

Head portion 24 of osteotome instrument 12 includes an externally threaded shaft 30 projecting therefrom generally parallel to handle shaft 22, onto which explant adapter 15 may be threaded. Spherical head 14 is connected to explant adapter 15 to secure spherical head 14 to osteotome instrument 12, as discussed in further detail below. Spherical head 14 includes a substantially spherical pivot surface 32.

Surgical kit 10 may include a plurality of spherical heads 14 of different diameters for use with acetabular cup liners of different sizes, each spherical head 14 including one or more osteotomes 16a, 16b sized for use with acetabular cups of different sizes. For example, acetabular cups and acetabular cup liners of larger sizes, which correspond with larger diameter femoral head components, require larger spherical heads 14 to be used with osteotome instrument 12 to remove larger acetabular cups from the acetabulum. Suitable spherical heads and osteotomes are selected depending upon the dimensions of the acetabular cup to be removed such that, when a corresponding spherical head and osteotome are attached to the instrument, the spacing between the osteotome blade and center of the spherical head corresponds to the spacing between the center of the recess in the acetabular cup liner and the rim of the acetabular cup.

Figure 2:
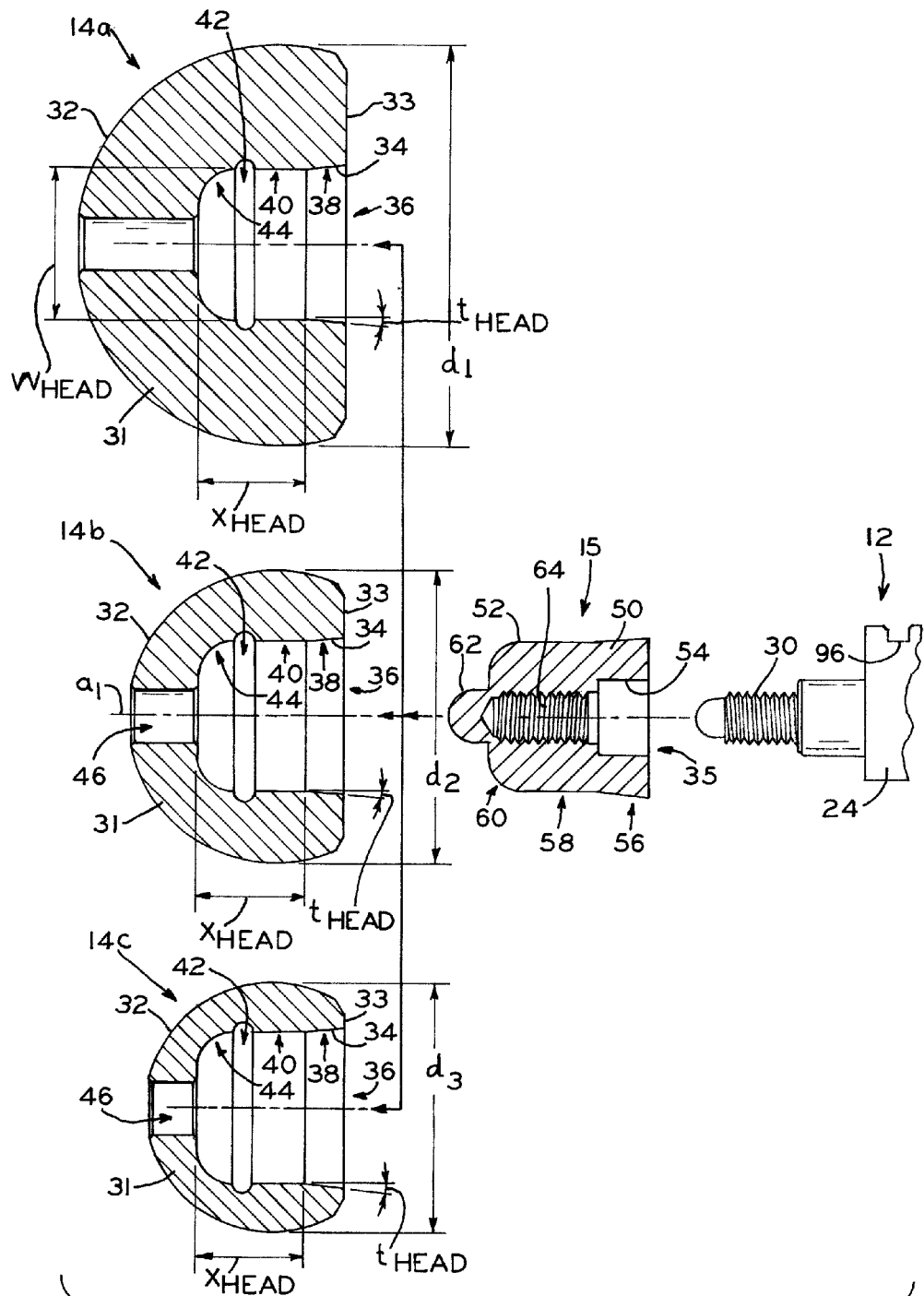
FIG. 2 is an exploded view of a threaded shaft of a head portion of an osteotome instrument, together with a plurality of different sized spherical heads and an explant adapter shown in section.

FIG. 2 illustrates a set of pivot elements, such as spherical heads 14a, 14b, 14c, explant adapter 15, and head portion 24 of osteotome instrument 12, according to an exemplary embodiment of the present disclosure. Exemplary pivot elements are shown herein and described below as spherical heads. Spherical heads 14a, 14b, 14c each generally include spherical head body 31 defining spherical head exterior wall 32 which is also the spherical head pivot surface, spherical head planar end wall 33, and spherical head interior wall 34. Spherical head exterior wall 32 and spherical head interior wall 34 respectively correspond to the exterior profile and the interior profile of spherical heads 14a, 14b, 14c. Spherical head interior wall 34 also defines cavity 36 of spherical heads 14a, 14b, 14c, cavity 36 extending through planar end wall 33. Spherical head interior wall 34 and cavity 36 are sized to receive explant adapter 15 therein. In the exemplary embodiment of FIG. 2, spherical heads 14a, 14b, 14c are illustrated as having identically dimensioned interior profiles, although the outside diameter of spherical heads 14a, 14b, 14c may vary, as discussed below. Interior walls 34 of heads 14a, 14b, 14c generally include frustoconical tapered portion 38, cylindrical portion 40, groove portion 42, and arcuate portion 44, which together generally define a bell-shaped interior profile of heads 14a, 14b, 14c. Further, cavity 36 includes access hole 46.

In one embodiment, a set of a plurality of different sized spherical heads can be provided to accommodate acetabular cups of different sizes. Referring to FIG. 2, outside diameter $d_1$, $d_2$, $d_3$ of spherical heads 14 could be relatively large, ranging from approximately 38 mm (approximately 1.496 inches) to approximately 60 mm (approximately 2.362 inches). For example, if twelve different sizes were to be used in the set of spherical heads, the outside diameter of the spherical heads could be 38 mm (1.496 inches), 40 mm (1.575 inches), 42 mm (1.654 inches), 44 mm (1.732 inches), 46 mm (1.811 inches), 48 mm (1.89 inches), 50 mm (1.969 inches), 52 mm (2.047 inches), 54 mm (2.126 inches), 56 mm (2.205 inches), 58 mm (2.283 inches), and 60 mm (2.362 inches). In one embodiment, as illustrated in FIG. 2 for example, outside diameter $d_1$ of head 14a is greater than outside diameter $d_2$ of head 14b, and outside diameter $d_2$ of head 14b is greater than outside diameter $d_3$ of head 14c. The set of a plurality of different sized spherical heads could include any desired number of different sized spherical heads.

Although the outside diameter of each of spherical heads 14a, 14b, 14c vary, the interior profile 34, i.e., tapered portion 38, cylindrical portion 40, groove portion 42, and arcuate portion 44, of all spherical heads 14a, 14b, 14c is identical. Advantageously, because each of the different sized spherical heads in the set have identical interior profiles 34, a single sized explant adapter 15 can be used to connect any one of the different sized spherical heads in the set to head portion 24 of osteotome instrument 12. Spherical heads 14a, 14b, 14c of an exemplary embodiment may advantageously be formed of various polymeric materials, i.e., plastics, including polyethylene and polyphenylsulfone, and may be disposeable.

Figure 3:
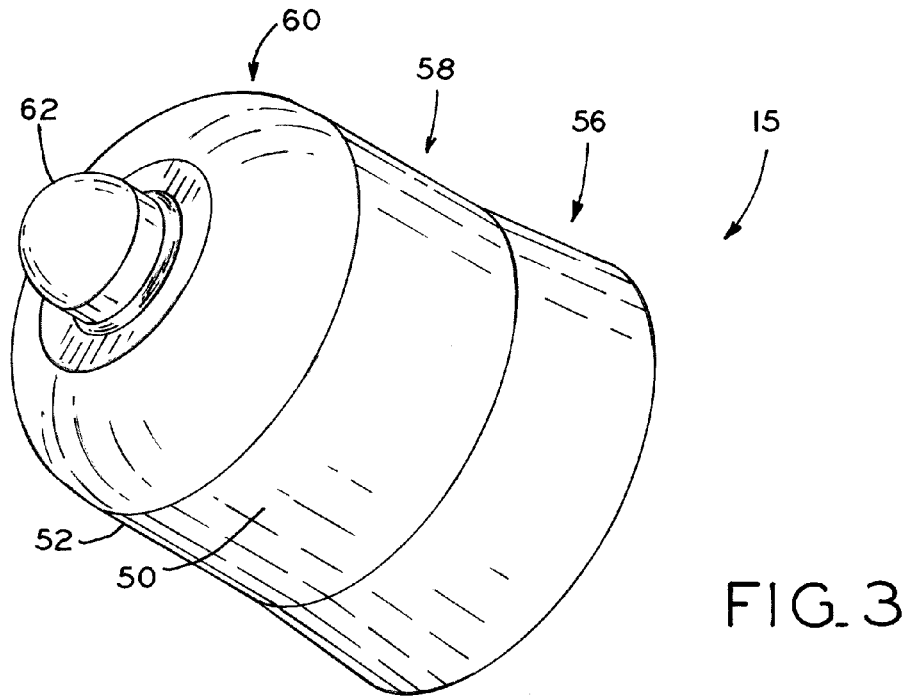
FIG. 3 is a perspective view of the explant adapter of FIG. 2.
Figure 4:
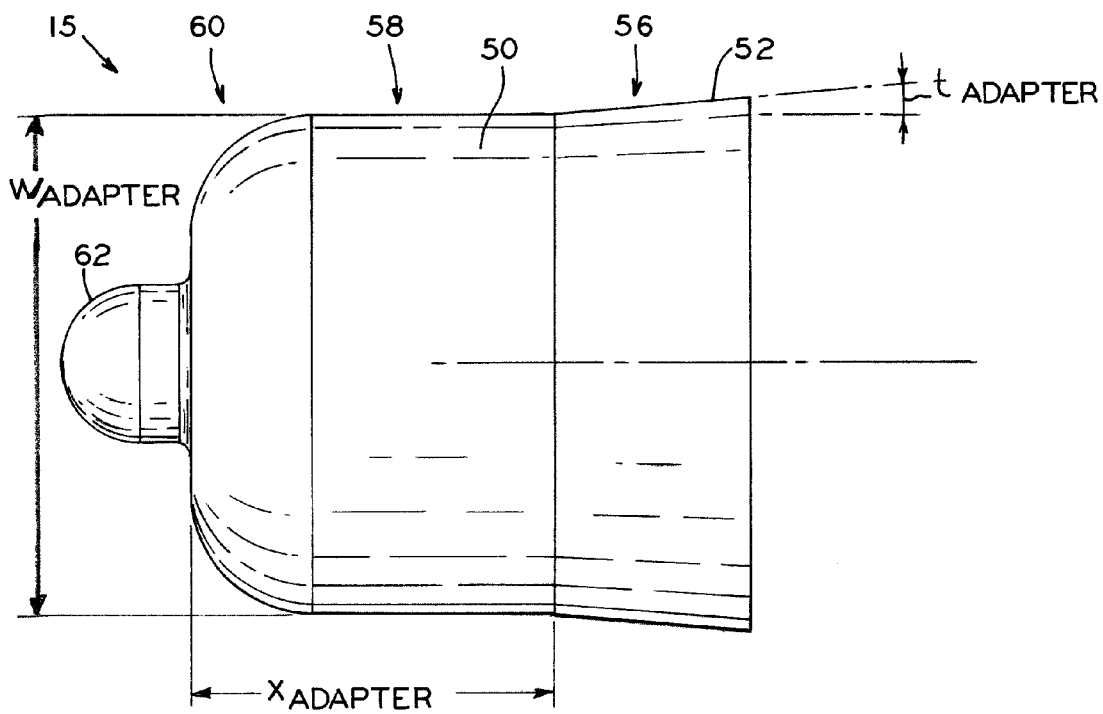
FIG. 4 is a side elevation view of the explant adapter of FIG. 2.

FIGS. 2-4 illustrate features of explant adapter 15 according to an exemplary embodiment of the present disclosure. Explant adapter 15 generally includes adapter body 50 defining adapter exterior wall 52 and adapter interior wall 54, respectively corresponding to the exterior profile and the interior profile of explant adapter 15. Referring to FIG. 2, interior wall 54 defines cavity 35, and includes an internally threaded portion or bore 64 to connect to externally threaded shaft 30 of head portion 24 of osteotome instrument 12. The exterior profile of exterior wall 52 generally includes frusto-conical tapered conical portion 56, cylindrical portion 58, arcuate portion 60, and protrusion 62. Explant adapter 15 of an exemplary embodiment is preferably made of a surgical grade material such as stainless steel, for example.

Referring to FIG. 2, in an exemplary embodiment, explant adapter 15 and spherical heads 14a, 14b, 14c are secured together using a taper lock and an interference connection to provide a secure fit therebetween, such that, as described below, with one of spherical heads 14a, 14b, 14c connected to explant adapter 15, rotation of handle shaft 22 of osteotome instrument 12 rotates explant adapter 15 and the spherical head 14a, 14b, 14c with little, if any, lost motion between the foregoing components. Explant adapter 15 and spherical heads 14a, 14b, 14c mate by means of complementary locking tapers on explant adapter tapered conical portion 56 of explant adapter 15 and tapered portion 38 of interior wall 34 of spherical heads 14a, 14b, 14c. Referring to FIGS. 2 and 4, in an exemplary embodiment, tapered portion 38 of interior wall 34 of spherical heads 14a, 14b, 14c and tapered conical portion 56 of explant adapter 15 have respective tapers $t_{head}$ and $t_{adapter}$ of approximately 5°, with an included angle of taper of 10°.

Referring to the central portion of FIG. 2, threaded shaft 30 of head portion 24 of osteotome instrument 12, explant adapter 15, and head 14b are coaxially aligned along central axis $a_1$. Referring to FIGS. 2 and 4, distance $x_{adapter}$ (FIG. 4), which is the combined axial length along central axis $a_1$ of cylindrical portion 58 and arcuate portion 60 of adapter 15, is sized to be shorter than the corresponding distance $x_{head}$ (FIG. 2), which is the combined axial length along central axis $a_1$ of cylindrical portion 40, groove portion 42, and arcuate portion 44 of interior wall 34 of heads 14a, 14b, 14c. This configuration ensures that the complementary locking tapers, i.e., tapered conical portion 56 of explant adapter 15 and tapered portion 38 of interior wall 34 of spherical heads 14a, 14b, 14c, lock before arcuate portion 60 explant adapter 15 bottoms out on arcuate portion 44 of heads 14a, 14b, 14c.

Additionally, explant adapter 15 and heads 14a, 14b, 14c are secured theretogether by an interference fit. Referring to FIG. 2, explant adapter conical portion 56, explant adapter cylindrical portion 58, and explant adapter arcuate portion 60, i.e., exterior profile 52 of explant adapter 15, are each sized and shaped to substantially correspond to the interior profile 34 of heads 14a, 14b, 14c. This interference fit between explant adapter 15 and heads 14a, 14b, 14c is achieved by sizing and shaping the two mating parts, i.e., exterior profile 52 of explant adapter 15 and interior profile 34 of heads 14a, 14b, 14c, so that exterior profile 52 of explant adapter 15 only slightly deviates dimensionally from interior profile 34 of heads 14a, 14b, 14c. For example, referring to FIGS. 2 and 4, in one embodiment, width W head of cylindrical portion 40 of head 14a may be sized to be approximately 0.908 inches (approximately 2.306 centimeters), while width $W_{adapter}$ of explant adapter cylindrical portion 58 can be sized to be approximately 0.902 inches (approximately 2.291 centimeters). This ensures an interference fit which secures explant adapter 15 and heads 14a, 14b, 14c together by a friction force after insertion of adapter 15 into a selected head 14a, 14b, 14c.

Referring to FIG. 2, as previously discussed, interior wall 54 of explant adapter 15 includes threaded portion 64 therein to allow explant adapter 15 to be threaded to shaft 30 of head portion 24 of osteotome instrument 12. Referring to FIGS. 2, 7, and 8, explant adapter 15 is secured to threaded shaft 30 of head portion 24 of osteotome instrument 12, and a selectively sized spherical head may be fitted on explant adapter 15, thereby securing explant adapter 15 and the selectively sized spherical head together by the taper lock and interference connection previously discussed. In this manner, adapter 15 allows a variety of different sized spherical heads to be secured to head portion 24 of osteotome instrument 12. Advantageously, once the taper lock and interference connection between explant adapter 15 and the particularly sized spherical head 14a, 14b, 14c is achieved, the selected head is rotationally secured to explant adapter 15.

Referring to FIGS. 2 and 6, spherical heads 14a, 14b, 14c each include access hole 46. When positioning explant adapter 15 on a particularly sized spherical head, protrusion 62 of explant adapter 15 is received within access hole 46. Advantageously, protrusion 62 of explant adapter 15 provides a means to center explant adapter 15 within cavity 36 of a desired spherical head when securing explant adapter 15 to a desired spherical head. Additionally, protrusion 62 provides increased stability to the fit between explant adapter 15 and a desired spherical head and further provides an easy lead in to access hole 46. In one embodiment, protrusion 62 of explant adapter 15 can also be sized and shaped to be received within access hole 46 with an interference fit. In another embodiment, protrusion 62 can be sized and shaped to be received within access hole 46 with a slight clearance. For example, in one embodiment, the diameter of protrusion 62 can be sized to be approximately 0.3 mm (approximately 0.01181 inch) smaller than the diameter of access hole 46.

Figure 5:
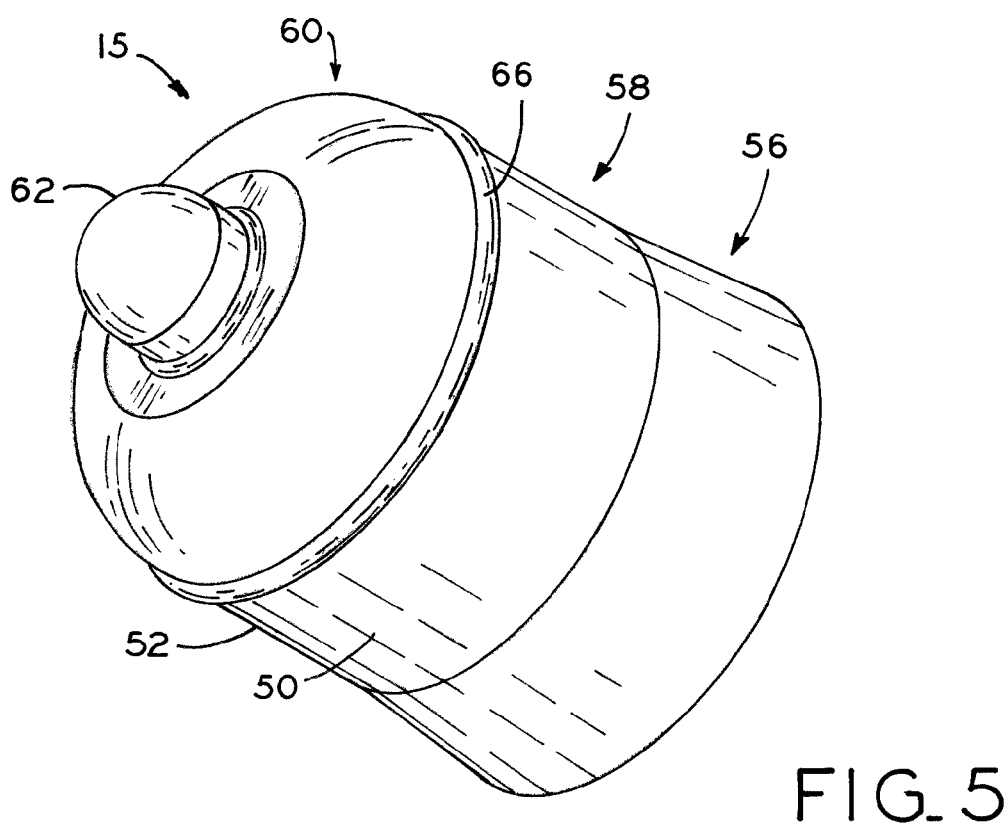
FIG. 5 is a perspective view of an explant adapter in accordance with another exemplary embodiment of the present disclosure.

Referring to FIG. 5, in another embodiment, explant adapter 15 may further include a deformable rib 66 extending circumferentially around a periphery of exterior wall 52 of explant adapter 15. In one embodiment, rib 66 extends around the periphery of exterior wall 52 of explant adapter 15 at a location where explant adapter cylindrical portion 58 and explant adapter arcuate portion 60 meet. Rib 66 is received within groove portion 42 of interior profile 34 of spherical heads 14a, 14b, 14c, and provides an additional securement mechanism between explant adapter 15 and spherical heads 14a, 14b, 14c. In other embodiments, an annular spring or o-ring (not shown) could be positioned around the periphery of exterior wall 52 of adapter 15, for receipt within groove portion 42 of interior profile 34 of spherical heads 14a, 14b, 14c to provide a further securement mechanism between adapter 15 and heads 14a, 14b, 14c.

Advantageously, because the single sized explant adapter 15 of the present disclosure allows each of a set of a plurality of different sized spherical heads to be securely connected to head portion 24 of osteotome instrument 12 via single adapter 15, a surgical kit is provided that has a reduced instrument case weight and the amount of surgical instrumentation needed during a surgical procedure is decreased.

Referring to FIG. 1, osteotomes 16a, 16b may be interchangeably connected to head portion 24 of instrument 12. An exemplary osteotome 16b is shown in FIGS. 13 and 14, and includes head portion 80 with curved blade 82b extending therefrom. Blade 82b includes end cutting surface 84 and a pair of side cutting surfaces 86. Head portion 80 of osteotome 16b also includes tooth 88, and slot 90 having semi-annular ledge 92.

Referring again to FIG. 1, osteotome instrument 12 further includes an osteotome-receiving recess 94 in head portion 24 thereof, having notch 96. Osteotome clamping screw 98 is disposed within recess 94 and threaded into head portion 24 of osteotome instrument 12. Osteotome clamping screw 98 is moveable between loosened and tightened positions, and further, may be retained by head portion 24 in the loosened position to prevent detachment of osteotome clamping screw 98 to simplify the interchanging of osteotomes 16a, 16b during a surgical procedure. As shown in FIG. 1, to attach an osteotome, such as osteotome 16a, for example, to instrument 12, osteotome 16a is placed within recess 94 such that osteotome clamping screw 98 is disposed within slot 90 of osteotome 16a, and tooth 88 of osteotome 16a is fitted within notch 96 of head portion 24, with blade clamping screw 98 in a loosened position. Thereafter, osteotome clamping screw 98 is tightened using torque wrench 18 and osteotome adapter 20 such that head 99 of osteotome clamping screw 98 engages ledge 92 of osteotome 16a to secure osteotome 16a to instrument 12. Torque wrench 18 may be adjusted to deliver a predetermined amount of torque to osteotome clamping screw 98, to prevent head 99 of osteotome clamping screw 98 from being tightened onto ledge 92 of osteotome 16a beyond a desired clamping force.

Figure 9:
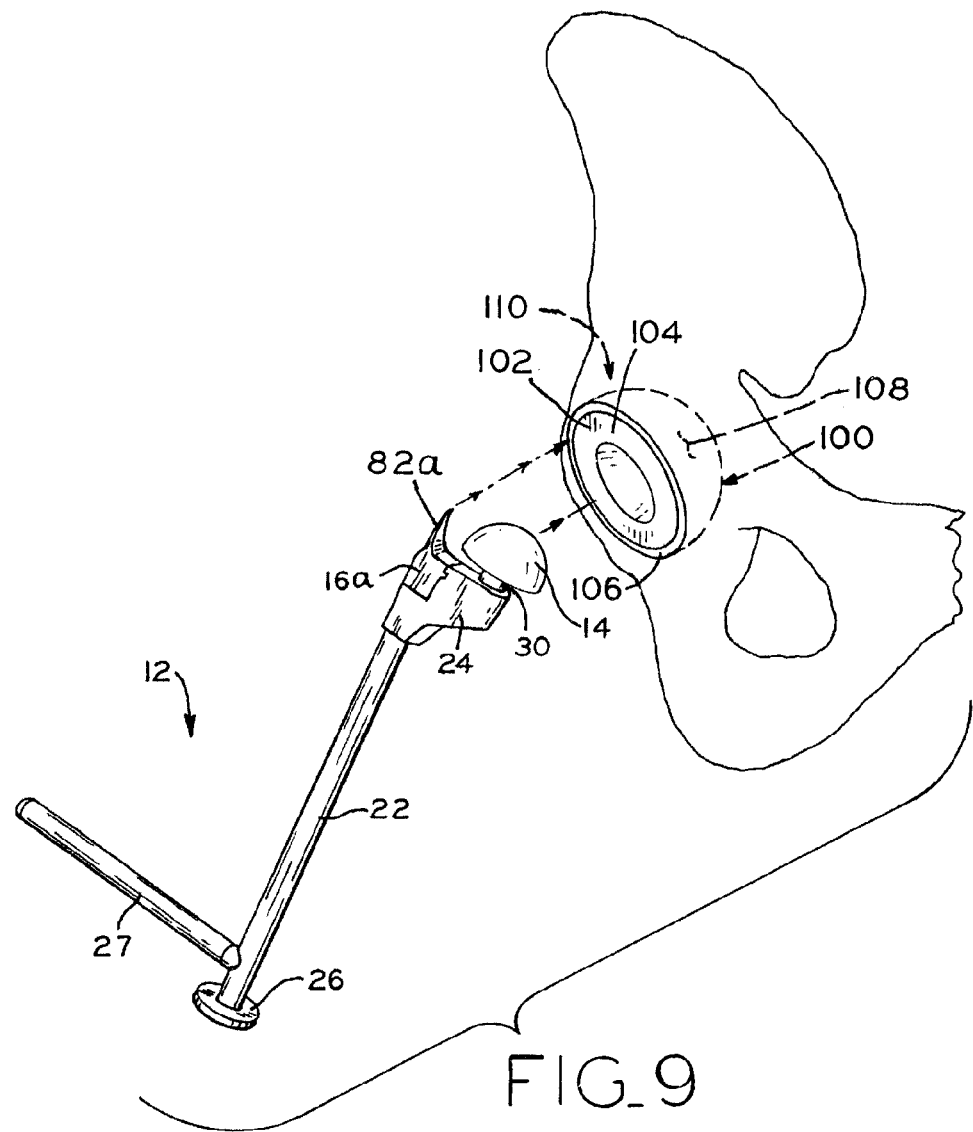
FIG. 9 is a perspective view of an acetabulum of a hip joint including an acetabular cup, and an osteotome instrument of the present disclosure being operatively coupled to the acetabular cup.
Figure 10:
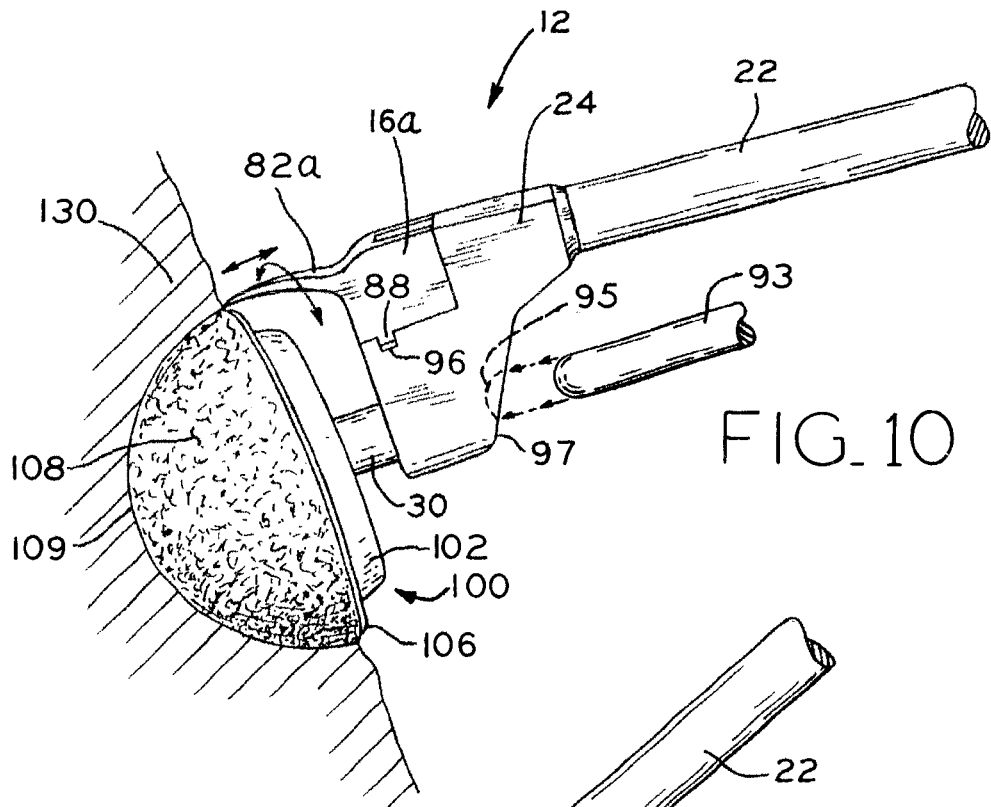
FIG. 10 is a partial sectional view through the acetabulum of FIG. 9 showing the spherical head of the osteotome instrument of FIG. 9 seated within the acetabular cup liner of the acetabular cup prior to cutting with an osteotome having a short blade.

Referring to FIGS. 9-12, the use of osteotome instrument 12 to remove an acetabular cup 100 will now be described. As shown in FIGS. 9 and 10, a first osteotome 16a having short blade 82a is attached to instrument 12 as described above. Then, spherical head 14 of osteotome instrument 12, attached to osteotome instrument 12 via explant adapter 15 as previously discussed, is seated within hemispherical recess 104 of liner 102 of acetabular cup 100, which is anchored in acetabulum 110. Rod 93 may be pressed against indentation 95 in rear side 97 of head portion 24 to aid in seating spherical head 14 within recess 104 of acetabular cup 100. As shown in FIG. 10, blade 82a of osteotome 16a is spaced a distance from the center of spherical head 14 which corresponds to the distance between the center of recess 104, or the center of spherical head 14, and rim 106 of acetabular cup 100, such that blade 82a is disposed closely adjacent outer hemispherical surface 108 of acetabular cup 100.

Figure 11:
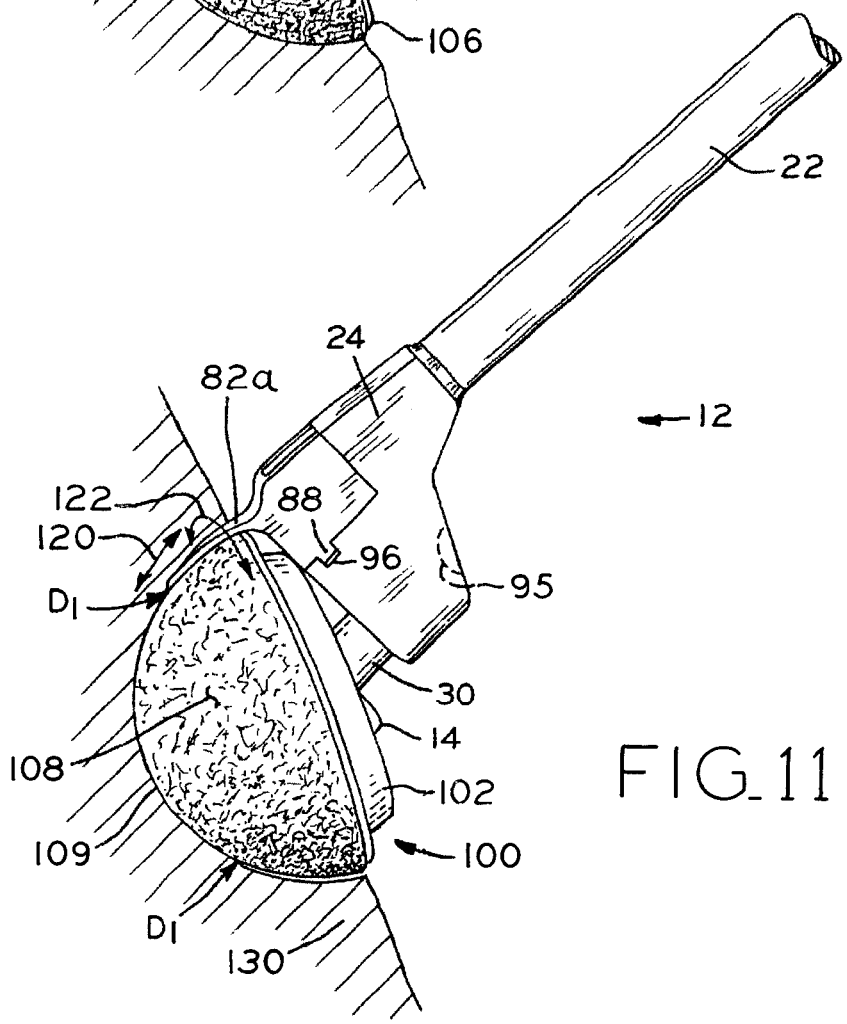
FIG. 11 is a partial sectional view showing the osteotome instrument of FIG. 10 in a pivoted position, the osteotome blade cutting bone adjacent the acetabulum to a first depth.

Handle shaft 22 of instrument 12 may be pivoted as shown in FIG. 11, such that blade 82a moves along the path of arrow 120, and end cutting surface 84 of blade 82a cuts bone 130 around outer hemispherical surface 108 of acetabular cup 100 in a direction from rim 106 toward apex 109 of acetabular cup 100. Thereafter, handle shaft 22 of instrument 12 may be pivoted in the reverse direction along the path of arrow 120 to withdraw blade 82a, wherein during such withdrawal, the engagement between tooth 88 of osteotome 16a within notch 96 in head portion 24 of instrument 12 prevents disengagement of osteotome 16a from instrument 12 in the event that blade clamping screw 98 is not sufficiently tightened. Impaction head 26 (FIGS. 1 and 9) may be struck with a mallet (not shown) as needed to drive blade 82a of osteotome 16a through bone 130 adjacent acetabulum 110.

Handle lever 27 (FIG. 9) of instrument 12 may be used to rotate instrument 12 such that blade 82a of osteotome 16a is moved to a position radially spaced from the first cut location, and handle shaft 22 may be pivoted to effect another cut from rim 106 toward apex 109 of acetabular cup 100. In this manner, several cuts may be made circumferentially about rim 106 of acetabular cup 100 to cut bone 130 away from acetabular cup 100 to a first depth $D_1$, which generally corresponds to the length of short blade 82a. Additionally, as shown by arrow 122 in FIG. 11, handle lever 27 of instrument 12 may be used to rotate blade 82a, striking handle lever 27 as necessary with a mallet (not shown), to make an orbital cut about the outer hemispherical surface 108 of acetabular cup 100 using side cutting surfaces 86 of blade 82a.

Advantageously, as may be seen in FIGS. 11 and 12, blade 82a is spaced closely adjacent outer hemispherical surface 108 of acetabular cup 100 during the cutting procedure described above, allowing bone 130 around acetabular cup 100 to be cut closely adjacent to acetabular cup 100, such that loss of bone 130 is minimized.

As shown in FIG. 12, a second osteotome 16b having long blade 82b may be attached to head portion 24 of instrument 12 as described above, wherein blade 82b extends to apex 109 of acetabular cup 100 when instrument 12 is pivoted along the direction of arrow 120. Instrument 12, with osteotome 16b attached thereto, is used in the same manner as described above to cut bone 130 surrounding acetabular cup 100 from first depth $D_1$ to a second depth $D_2$ at apex 109 of acetabular cup 100. After bone 130 surrounding acetabular cup 100 is cut away therefrom, acetabular cup 100 may be removed from acetabulum 110, leaving an intact, hemispherical recess in acetabulum 110 into which a replacement acetabular cup (not shown) may be easily fitted.

While this disclosure has been described as having an exemplary design, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An instrument for removing an acetabular cup from an acetabulum, said instrument comprising:
    a handle;
    a blade connectable to said handle;
    an adapter connectable to said handle in spaced relationship from said blade, said adapter having an exterior profile that includes a protrusion, an arcuate portion, a first cylindrical portion, and a first frustoconical portion, wherein the protrusion extends distally from the arcuate portion and the arcuate portion extends distally from the cylindrical portion; and
    a pivot element connectable to said adapter and dimensioned to be received within an acetabular cup, said pivot element having an interior profile including a second cylindrical portion, a second frustoconical portion, and a cavity in which said protrusion is receivable, said first and second frustoconical portions dimensioned complementary to one another to form a taper lock and said first and second cylindrical portions dimensioned to interference fit with one another upon receipt of said adapter within said pivot element.

2. The instrument of claim 1, wherein said adapter is made of metal and said pivot element is made of a polymeric material.

3. The instrument of claim 1, wherein said adapter is connectable to said handle by threaded engagement of an externally threaded shaft of said instrument into an internally threaded bore of said adapter.

4. The instrument of claim 1, wherein said pivot element has a diameter between 38 mm and 60 mm.

5. The instrument of claim 1, wherein the pivot element includes a groove portion extending circumferentially around the interior profile and wherein a rib extending circumferentially around the adapter at a location distal from the first cylindrical portion is received within the groove portion when the pivot element is connected to the adapter.

6. The instrument of claim 1, wherein the adapter further includes
 a rib that extends circumferentially around the adapter at a location where the first cylindrical portion and the first arcuate portion meet, and
 wherein the interior profile of the pivot element includes
  a groove portion,
  a second arcuate portion, and
  an access hole,
 wherein the access hole extends distally from the second arcuate portion and the groove portion extends circumferentially around the interior profile of the pivot element at a location where the second arcuate portion and the second cylindrical portion meet and wherein the second arcuate portion extends distally from the second frustoconical portion and wherein the protrusion is receivable within the access hole and has a smaller diameter than the access hole.

7. An instrument for removing an acetabular cup from an acetabulum, said instrument comprising:
 a handle;
 a blade connectable to said handle;
 an adapter connectable to said handle in spaced relationship from said blade, said adapter having an exterior profile that includes a protrusion, an arcuate portion, a first cylindrical portion, and a first frustoconical portion, wherein the protrusion extends distally from the arcuate portion and the arcuate portion extends distally from the first cylindrical portion; and
 a pivot element connectable to said adapter and dimensioned to be received within an acetabular cup, said pivot element having an interior profile dimensioned complementary to said exterior profile of said adapter for receipt of said adapter within said pivot element, said pivot element further including a cavity in which said protrusion is receivable.

8. The instrument of claim 7, wherein the first cylindrical portion extends distally from the first frustoconical portion and wherein the interior profile of said pivot element includes a second frustoconical portion, said first and second frustoconical portions of said adapter and said pivot element, respectively, dimensioned complementary to one another to form a taper lock upon connection of said adapter to said pivot element.

9. The instrument of claim 8, wherein said interior profile of said pivot element includes a second cylindrical portion, said first and second cylindrical portions of said adapter and said pivot element, respectively, dimensioned to interference fit with one another upon connection of said adapter to said pivot element.

10. The instrument of claim 7, wherein said adapter is made of metal and said pivot element is made of a polymeric material.

11. The instrument of claim 7, wherein said pivot element has a diameter between 38 mm and 60 mm.

12. A kit for removing an acetabular cup from an acetabulum, said kit comprising:
 an instrument having a handle;
 a blade connectable to said instrument;
 a metal adapter connectable to said instrument in spaced relationship from said blade, said adapter having an exterior profile that includes a protrusion, an arcuate portion, a first cylindrical portion, and a first frustoconical portion, wherein the protrusion extends distally from the arcuate portion and the arcuate portion extends distally from the first cylindrical portion;
 a first pivot element made of a polymeric material and connectable to said adapter, said first pivot element having a first diameter and dimensioned to be received within an acetabular cup, said first pivot element defining an interior profile, said exterior profile of said adapter dimensioned for receipt within said interior profile of said first pivot element; and
 a second pivot element made of a polymeric material and connectable to said adapter, said second pivot element having a second diameter different from said first diameter and dimensioned to be received within an acetabular cup, said second pivot element defining an interior profile, said exterior profile of said adapter dimensioned for receipt within said interior profile of said second pivot element and wherein the interior profile of at least one of the first and second pivot elements includes an access hole and the protrusion is receivable within the access hole.

13. The kit of claim 12, wherein said interior profiles of said first and second pivot elements are indentical.

14. The kit of claim 12, wherein each of said interior profiles of said first and second pivot elements includes an interior frustoconical tapered wall, said first frustoconical portion of the adapter and said interior frustoconical tapered walls dimensioned complementary to one another to form a taper lock upon engagement of said adapter with one said first and second pivot elements.

15. The kit of claim 12, wherein said exterior profile of said adapter and said interior profile of each of said first and second pivot elements are dimensioned to interference fit with one another upon respective engagement of said adapter with one said first and second pivot elements.

16. The kit of claim 12, wherein said interior profile of at least one of said first and second pivot elements include a cylindrical portion and a frustoconical portion.

17. The kit of claim 12, wherein said first and second diameters of said first and second pivot elements, respectively, are each between 38 mm and 60 mm.

18. The kit of claim 12, wherein the protrusion has a smaller diameter than the access hole.

* * * * *

UNITED STATES PATENT AND TRADEMARK OFFICE
CERTIFICATE OF CORRECTION

PATENT NO. : 8,834,480 B2
APPLICATION NO. : 13/350027
DATED : September 16, 2014
INVENTOR(S) : Hudak, Jr. et al.

It is certified that error appears in the above-identified patent and that said Letters Patent is hereby corrected as shown below:

IN THE CLAIMS:

In column 8, line 53, in Claim 1, after "the", insert --first--, therefor

In column 10, line 38, in Claim 13, delete "indentical." and insert --identical.--, therefor Signed and Sealed this
Ninth Day of December, 2014

Michelle K. Lee
*Deputy Director of the United States Patent and Trademark Office*